United States Patent
Watanabe et al.

(10) Patent No.: US 6,969,774 B2
(45) Date of Patent: Nov. 29, 2005

(54) METHOD FOR PRODUCING METHACRYLIC ACID

(75) Inventors: Seigo Watanabe, Hiroshima (JP); Motomu Oh-Kita, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 8 days.

(21) Appl. No.: 10/148,171

(22) PCT Filed: Dec. 7, 2000

(86) PCT No.: PCT/JP00/08637

§ 371 (c)(1),
(2), (4) Date: May 31, 2002

(87) PCT Pub. No.: WO01/42184

PCT Pub. Date: Jun. 14, 2001

(65) Prior Publication Data

US 2003/0004374 A1 Jan. 2, 2003

(30) Foreign Application Priority Data

Dec. 10, 1999 (JP) .......................................... 11/351263

(51) Int. Cl.$^7$ ............................................ C07C 51/235
(52) U.S. Cl. ....................... 562/532; 562/523; 562/531; 562/598
(58) Field of Search ................................ 562/512, 523, 562/531, 532, 534, 535

(56) References Cited

U.S. PATENT DOCUMENTS

| 4,954,650 A | * | 9/1990 | Abe et al. ................... 562/534 |
| 5,206,431 A | | 4/1993 | Hashiba et al. |

FOREIGN PATENT DOCUMENTS

| EP | 441312 | 8/1991 |
| JP | 57-120547 | 7/1982 |
| JP | 7-10802 | 1/1995 |
| JP | 8-3093 | 1/1996 |

* cited by examiner

*Primary Examiner*—Johann Richter
*Assistant Examiner*—Karl Puttlitz

(57) ABSTRACT

In a method for synthesizing methacrylic acid by using a fixed bed tube type reactor provided with a catalyst bed into which a solid oxidation catalyst is filled and with a heat medium bath and by flowing a raw material gas containing methacrolein and oxygen through the catalyst bed, the catalyst bed does not have any sections in which a temperature difference between the heat medium bath and the catalyst bed ($\Delta T$) exceeds 35° C., and two or more high temperature zones in which each $\Delta T$ is 15 to 35° C. are provided. According to this method, mathacrylic acid can be manufactured in higher yields.

11 Claims, No Drawings

METHOD FOR PRODUCING METHACRYLIC ACID

TECHNICAL FIELD

This invention relates to a method for manufacturing methacrylic acid by vapor phase catalytic oxidation of methacrolein with molecular oxygen in the presence of a solid oxidation catalyst using a fixed bed tube type reactor.

BACKGROUND ART

There have been many suggestions of catalysts which are used in manufacturing methacrylic acid by a vapor phase catalytic oxidation reaction of methacrolein (this vapor phase catalytic oxidation reaction will be referred to merely as "oxidation reaction," unless otherwise specified hereinafter). These suggestions are mainly related to elements constituting the catalysts and a ratio of the elements.

The oxidation reaction causes heat accumulation in a catalyst bed because this reaction is an exothermic reaction. Locally abnormal high temperature zones resulting from excessive heat accumulation are known as hot spots, in which yields are reduced by the excessive oxidation reaction. Thus, when conducting the oxidation reaction on an industrial scale, occurrence of the hot spots is a significant problem, and particularly in the case where a concentration of methacrolein in a raw material gas is increased in order to increase productivity, the hot spots tend to easily occur, so that the reaction conditions are required to be largely restricted under the present circumstances.

Therefore, it is very important to control the temperature at the hot spot section for producing methacrylic acid in high yield on an industrial scale. In addition, especially in case of using a molybdenum containing solid oxidation catalyst, it is important to prevent the occurrence of the hot spots because the molybdenum moiety is easy to be sublimated.

Several suggestions have been made as for a method for controlling the temperature at the hot spot section. For example, Japanese Patent Application Laid-Open No. 4-210937 discloses a method in which a plurality of catalysts having different activities are filled in such a manner that their activities become gradually higher from an inlet side for a raw material gas toward an outlet side, then the raw material gas containing methaclorein and oxygen is flown through this catalyst bed. Japanese Patent Application Laid-Open No. 8-92154 discloses a method in which, when acrolein is subjected to vapor phase oxidation using a multi-tube type fixed bed reactor provided with a heat medium bath to produce acrylic acid, a flow of the heat medium is controlled so that the temperature of the heat medium bath is raised by 2 to 10° C. between the inlet section and the outlet section.

However, these methods are only for the purpose of decreasing the temperature of the hot spot section, and are the methods which merely reduce a temperature difference (ΔT) between the heat medium bath and the catalyst bed in one hot spot section to some extent. That is, according to these methods, heat generation caused by oxidation reaction has not been actively controlled within the catalyst bed, so that, for example when a methacrolein concentration is further increased in order to increase productivity, heat generation at the hot spot section becomes remarkable. Hence, the reaction conditions are still required to be largely restricted. That is, under the present circumstances, the yield of methacrylic acid which is industrially acceptable has not been obtained when a concentration of methacrolein is increased to a level which is industrially acceptable.

DISCLOSURE OF THE INVENTION

Therefore, an object of the present invention is to provide a method for manufacturing methacrylic acid by vapor phase catalytic oxidation of methacrolein with molecular oxygen in the presence of a solid oxidation catalyst in a fixed bed tube type reactor, wherein metharylic acid is manufactured in a higher yield.

The present invention is a method for manufacturing methacrylic acid characterized in that methacrylic acid is synthesized by filling a solid oxidation catalyst into a fixed bed tube type reactor provided with a heat medium bath and by flowing a raw material gas containing methacrolein and oxygen through the catalyst bed and the catalyst bed does not have any sections in which a temperature difference between the heat medium bath and the catalyst bed (ΔT= catalyst bed temperature −heat medium bath temperature) exceeds 35° C. and two or more high temperature zones in which each ΔT thereof is 15 to 35° C. are provided.

BEST MODE FOR CARRYING OUT THE INVENTION

According to the present invention, a reaction for synthesizing methacrylic acid is carried out using a fixed bed tube type reactor provided with a heat medium bath. Although there are no limitations on the heat medium used herein, molten salts containing potassium nitrate and sodium nitrite are typically employed. There are also no limitations on the tube type reactor, but on an industrial scale, it is preferable to use a multi-tube type reactor provided with several thousands to several ten thousands of reaction tubes each of which has an inner diameter of 20 to 30 mm and each of which is surrounded by a heat medium bath.

In the present invention, the solid oxidation catalyst used herein is not particularly restricted as long as the catalyst is a solid catalyst for use in this oxidation reaction. Phosphorus and molybdenum containing composite oxides or the like which are previously known can be used, and the composite oxides represented by the following formula (1) are preferred:

$$Mo_aP_bCu_cV_dX_eY_fO_g \quad (1)$$

In the formula (1), Mo, P, Cu, V and O represent molybdenum, phosphorus, copper, vanadium, and oxygen, respectively, X represents at least one element selected from a group consisting of iron, cobalt, nickel, zinc, magnesium, calcium, strontium, barium, titanium, chromium, tungsten, manganese, silver, boron, silicon, tin, lead, arsenic, antimony, bismuth, niobium, tantalum, zirconium, indium, sulfur, selenium, tellurium, lanthanum, and cerium, and Y represents at least one element selected from a group consisting of potassium, rubidium, cesium, and thallium. In the above formula (1), a, b, c, d, e, f, and g represent atomic ratios of the respective elements. When a=12, $0.1 \leq b \leq 3$, $0.01 \leq c \leq 3$, $0.01 \leq d \leq 3$, $0 \leq e \leq 3$, $0.01 \leq f \leq 3$, and g is an atomic ratio of oxygen which is required to satisfy a valence of the above described each component. Particularly preferable atomic ratios of the respective elements are $0.2 \leq b \leq 2$, $0.04 \leq c \leq 1$, $0.1 \leq d \leq 2$, $0 \leq e \leq 2$, and $0 \leq f \leq 2$, when a=12.

A method for preparing a catalyst used in the present invention is not particularly limited, and the previously well-known various methods can be used unless the components thereof extremely unevenly distributed within a catalyst.

Raw materials used for preparing the catalyst are not particularly limited, and nitrates, carbonates, acetates, ammonium salts, oxides, halides or the like of each element can be employed in combination. For example, ammonium paramolybdate, molybdenum trioxide, molybdic acid, molybdenum chloride or the like can be used as a raw material for molybdenum.

Although a catalyst used in the present invention may be carrier-free, it is possible to use a catalyst supported on an inactive carrier such as silica, alumina, silica-alumina, or silicon carbide, or a catalyst diluted by these carriers.

In the present invention, a catalyst bed means a space section containing at least a catalyst within a reaction tube of a fixed bed tube type reactor. That is, a catalyst bed is not only a space which is filled only with a catalyst but also a space section in which the catalyst is diluted with the inactive carrier or the like. However, space sections at both ends of the reaction tube into which no substance is filled or space sections into which only inactive carriers or the like are filled are not included to the catalyst bed, because these sections substantially do not contain any catalysts.

In the present invention, when synthesizing methacrylic acid by filling a solid oxidation catalyst into a fixed bed tube type reactor provided with a heat medium bath and by flowing a raw material gas containing methacrolein and oxygen through the catalyst bed, it is important to provide two or more high temperature zones within the catalyst bed in which the temperature difference between the heat medium bath and the catalyst bed ($\Delta T$) is 15 to 35° C. A smaller maximum value of $\Delta T$ in the catalyst bed is preferred, and the maximum value $\Delta T$ should be not larger than 35° C. because if a value of $\Delta T$ becomes too larger, an excessive oxidation reaction causes a reduction in selectivity, which leads to a reduction of the yields, and there is also a possibility of degradation and alteration of the catalyst property due to thermal load. An oxidation reaction in the present invention is an exothermic reaction, so that it is inevitable that a $\Delta T$ which is a certain degree of magnitude is produced. However, controlling the conditions in such a manner that two or more high temperature zones in which each $\Delta T$ is 15° C. or more are provided, it is possible to avoid producing a locally abnormal high temperature zone concentrated in one region. As a matter of course, zones each $\Delta T$ of which is less than 15° C. should exist among these respective high temperature zones.

Methods for controlling the conditions in such a manner that two or more high temperature zones are provided are not particularly limited and include, for example, such as a method in which catalysts are filled into respective reaction zones provided by dividing a space within a reaction tube into two or more regions in its tube axial direction and a length of each reaction zone in its tube axial direction is adjusted and the catalytic activity per unit volume in each reaction zone is controlled. In this case, the methods for controlling the catalytic activity per unit volume include, for example, such as a method for controlling a dilution ratio when the catalyst is diluted with an inactive carrier, and a method for controlling by using other catalysts having different activities which are obtained by modifying a catalyst composition or a preparing process thereof.

It is preferable that the two or more high temperature zones in which each $\Delta T$ is within a range of 15 to 35° C. are provided in a catalyst bed in such a manner that a distance between a first high temperature zone and a second high temperature zone from an inlet side for the raw material gas is 0.2 to 0.9 times the overall length of the catalyst bed, and particularly, it is preferable that the distance should be 0.25 to 0.8 times the overall length of the catalyst bed. A proportion of the catalyst effectively acting in the whole catalyst filled into the reactor tends to increase as the ratio of the distance between the high temperature zones to the overall length of the catalyst bed becomes smaller, whereas an yield of methacrylic acid tends to be higher and the possibility resulting in the degradation and alteration of the catalyst tends to be reduced as the above described ratio becomes larger. When there are three or more high temperature zones, the distance between the two adjacent high temperature zones may be 0.2 to 0.9 times the overall length of the catalyst bed, and particularly 0.25 to 0.8 times the overall length thereof. The number of the high temperature zones is typically five or less, and practically two or three are preferable.

And the distance between the high temperature zones represents a distance between the points at each of which the $\Delta T$ is maximum in the high temperature zone.

A position of the first high temperature zone (a position wherein the $\Delta T$ is maximum within this high temperature zone) is preferable at a distance of 0 to 0.7 times the overall length of the catalyst bed from the inlet for the raw material gas, and it is particularly preferable at a distance of 0.1 to 0.5 times the overall length of the catalyst bed from the above described inlet.

Usually, minute peaks and valleys can be seen on the $\Delta T$ curve which is in a tube axial direction, because of slightly nonuniform distribution of the filled catalyst. Hence, when determining a range of the high temperature zone, noise caused by the peaks and valleys is reduced by determining a mean $\Delta T$ for the measured $\Delta T$s around the certain measurement position within a range of 0.005 times, preferably 0.01 times, the overall length of the catalyst bed. Even if an exothermic peak which satisfies a requirement of the high temperature zone is observed at the measured $\Delta T$, in the case where the requirement of the high temperature zone is not satisfied when based on the mean $\Delta T$, the exothermic peak should not be taken as the high temperature zone.

In the present invention, $\Delta T$ in the catalyst bed means a difference between temperature at a certain measurement position within the catalyst bed and temperature of a heat medium bath around the position. Although there is a possibility of nonuniform distribution of heat medium temperatures within the heat medium bath depending on, such as, a reactor configuration, reaction conditions, and a flowing state of the heat medium, there is no problem in treating the mean temperature of the heat medium bath as a heat medium bath temperature in the case where a degree of the nonuniform distribution is small. However, in the case where the degree is not small, it is required to determine $\Delta T$ by measuring the heat medium temperature at each position.

Further, methods for measuring temperatures in the catalyst bed include, for example, a method in which, prior to filling a catalyst, protective tubes are placed in the tube type reactor and a thermocouple is inserted into the respective protective tubes to measure the temperatures at the respective positions during reaction. In this method, a position to place the protective tube is preferably a center of a section which is normal to the tube axial direction of the reaction tube, and a length of the protective tube is required to be longer than that of the catalyst bed. This method is preferable because the temperatures at any positions within the catalyst bed can be conveniently measured. In addition, in case of using a multi-tube type reactor which is industrially employed, it is actually impossible to measure the temperatures of the catalyst beds of all reaction tubes, so that some of the reaction tubes which represent the entire reactor will be actually subjected to this measurement.

In practice of the present invention, a concentration of methacrolein in a raw material gas can be varied within a wide range, but it is appropriate to be in a range of 1 to 20 volume %, and particularly preferable to be in a range of 3 to 8 volume %.

It is economically advantageous to use air as a source of oxygen, but air enriched with pure oxygen may be used if necessary. A concentration of oxygen in the raw material gas is preferably 0.3 to 4 moles relative to one mole of methacrolein, particularly it is preferable to be 0.4 to 3 moles. The raw material gas may contain a little amount of impurities such as lower saturated hydrocarbyl aldehyde which do not substantially influence on a primary reaction and may also be diluted by adding inactive gases such as nitrogen, steam, and carbon dioxide.

A reaction pressure for oxidation reaction can be varied from an atmospheric pressure to several atmospheres. The heat medium bath temperature which is a reaction temperature is preferable 230 to 450° C., and particularly preferable 250 to 400° C. A space velocity of a raw material gas is preferable 300 to 3000 $hr^{-1}$, and particularly preferable 500 to 2000 $hr^{-1}$.

EXAMPLES

The present invention will now be further described in detail by examples. In the examples and comparative examples, "part(s)" means part(s) by weight. A composition of a catalyst was determined from the charged amounts of raw materials of catalyst components. As a heat medium of a reactor, a molten salt composed of 50 mass % of potassium nitrate and 50 mass % of sodium nitrite was used. An analysis of reaction raw materials and products was carried out by gas chromatography.

In addition, a conversion of methacrolein, a selectivity of produced methacrylic acid, and a one-pass yield of methacrylic acid are respectively defined as follows.

Conversion of methacrolein (%)=(B/A)×100

Selectivity of methacrylic acid (%)=(C/B)×100

One-pass yield of methacrylic acid (%)=(C/A)×100

In the above definitions, A is the number of moles of supplied methacrolein, B is the number of moles of reacted methacrolein, and C is the number of moles of produced methacrylic acid.

Example 1

100 parts of ammonium paramolybdate, 2.8 parts of ammonium metavanadate, and 9.2 parts of cesium nitrate were dissolved into 300 parts of pure water. A solution of 8.2 parts of 85 mass % phosphoric acid in 10 parts of pure water and a solution of 1.1 parts of telluric acid in 10 parts of pure water were added to above solution with stirring, and temperature was raised to 95° C. with stirring. Then, a solution of 3.4 parts of copper nitrate, 7.6 parts of ferric nitrate, 1.4 parts of zinc nitrate, and 1.8 parts of magnesium nitrate in 80 parts of pure water was added. Further, this mixture was stirred for 15 minutes at 100° C., and an obtained slurry was dried using a spray dryer.

Two parts of graphite were added to 100 parts of the obtained dried substance and mixed with each other, then pressed into ring tablets which were 5 mm in outer diameter, 2 mm in inner diameter, and 3 mm in length by using a tabletting machine. The tablets were calcined at 380° C. for 5 hours while flowing air, then a catalyst 1 was obtained. The composition of the catalyst 1, represented by an atomic ratio excluding oxygen, was as follows:

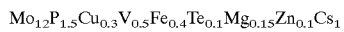

$Mo_{12}P_{1.5}Cu_{0.3}V_{0.5}Fe_{0.4}Te_{0.1}Mg_{0.15}Zn_{0.1}Cs_1$

A mixture of 370 mL of the catalyst 1 and 130 mL of alumina balls having an outer diameter of 5 mm was filled into an inlet part for a raw material gas of a steel made fixed bed tube type reactor having an inner diameter of 25.4 mm which was provided with a heat medium bath, and 1000 mL of the catalyst 1 was filled into an outlet part of the above described reactor. In this case, a length of the catalyst bed was 3005 mm. A raw material gas consisting of 6.5 volume % of methacrolein, 11 volume % of oxygen, 10 volume % of steam, and 72.5 volume % of nitrogen was passed through this catalyst bed at a space velocity of 1000 $hr^{-1}$ and at a reaction temperature (a heat medium bath temperature) of 290° C.

Upon measuring a temperature of the catalyst bed in this case, a first high temperature zone in which a maximum temperature point was 300 mm from an end of the inlet side for the raw material gas and a second high temperature zone in which a maximum temperature point was 1200 mm from the end of the inlet side for the raw material gas were observed. That is, a ratio of a distance between the above two high temperature zones to the length of the catalyst bed was 0.30. In addition, $\Delta T$ at the position of the maximum temperature in the first high temperature zone was 21° C., and $\Delta T$ at the position of the maximum temperature in the second high temperature zone was 19° C. Further, $\Delta T$ at a position 1000 mm from the end of the inlet side for the raw material gas was 12° C.

Table 1 shows analytical results for the reaction products which were collected.

Comparative Example 1

A mixture of 620 mL of the catalyst 1 and 130 mL of alumina balls having an outer diameter of 5 mm was filled into an inlet part for a raw material gas of the same fixed bed tube type reactor as used in Example 1, and 750 mL of the catalyst 1 was filled into an outlet part of this reactor. A length of the catalyst bed in this case was 3005 mm. The same raw material gas as used in Example 1 was passed through this catalyst bed under the same conditions.

Then measuring the temperature of the catalyst bed, only one high temperature zone was observed in which the maximum temperature point was 400 mm from the end of the inlet side for the raw material gas. In addition, $\Delta T$ at the maximum temperature of this high temperature zone was 31° C.

Table 1 shows results of analysis of the reaction product.

Comparative Example 2

1500 mL of the catalyst 1 was filled into the same reactor as used in Example 1. A length of the catalyst bed at this time was 3005 mm. The same raw material gas as used in Example 1 was passed through this catalyst bed under the same conditions.

Then measuring the temperature of the catalyst bed, only one high temperature zone was observed in which the maximum temperature point was 200 mm from the end of the inlet side of the raw material gas. In addition, $\Delta T$ at the maximum temperature of this high temperature zone was 40° C.

Table 1 shows results of analysis of the reaction product.

Comparative Example 3

1370 mL of the catalyst 1 was filled into the same reactor as used in Example 1. A length of the catalyst bed at this time was 2745 mm. The same raw material gas as used in Example 1 was passed through this catalyst bed under the same conditions.

Then measuring the temperature of the catalyst bed, only one high temperature zone was observed in which the maximum temperature point was 200 mm from the end of the inlet side of the raw material gas. In addition, ΔT at the maximum temperature of this high temperature zone was 40° C.

Table 1 shows results of analysis of the reaction product.

Comparative Example 4

A mixture of 220 mL of the catalyst 1 and 130 mL of alumina balls having an outer diameter of 5 mm was filled into an inlet part for a raw material gas of the same reactor as used in Example 1, and 1150 mL of the catalyst 1 was filled into an outlet part of this reactor. A length of the catalyst bed at this time was 3005 mm. The same raw material gas as used in Example 1 was passed through this catalyst bed under the same conditions.

Upon measuring a temperature of the catalyst bed at this time, a first high temperature zone in which the maximum temperature point was 250 mm from an end of the inlet side for the raw material gas and a second high temperature zone in which the maximum temperature point was 830 mm from the end of the inlet side of the raw material gas were observed. That is, a ratio of a distance between the above two high temperature zones to the length of the catalyst bed was 0.19. In addition, ΔT at the maximum temperature of the first high temperature zone was 16° C., and ΔT at the maximum temperature of the second high temperature zone was 37° C. Further, ΔT at a position 700 mm from the end of the inlet side of the raw material gas was 10° C.

Table 1 shows results of analysis of the reaction product.

Example 2

100 parts of molybdenum trioxide, 3.2 parts of vanadium pentaoxide, and 6.7 parts of 85 mass % phosphoric acid were mixed with 800 parts of pure water. After stirring this mixture for three hours while heating at reflux, 0.5 part of copper oxide, 0.7 part of boric acid, and 1.2 parts of germanium dioxide were added to the mixture, then the mixture was stirred again for two hours while heating at reflux. The obtained slurry was cooled to 50° C., and a solution of 11.2 parts of cesium bicarbonate in 30 parts of pure water was added to this slurry and stirred for 15 minutes. Then, a solution of 10 parts of ammonium nitrate in 30 parts of pure water was added to the slurry and further stirred for 15 minutes, and the obtained slurry containing catalyst components was dried using a spray dryer.

Two parts of graphite were added to 100 parts of the obtained dried substance and mixed with each other, then pressed into ring tablets which had an outer diameter of 5 mm, an inner diameter of 2 mm, and a length of 3 mm using a tabletting machine. The tablets were calcined at 380° C. for 5 hours while flowing air, then a catalyst 2 was obtained. The composition of the catalyst 2 represented by an atomic ratio, exclusive of oxygen, was

$Mo_{12}P_1Cu_{0.1}V_{0.6}Ge_{0.2}B_{0.2}Cs_1$

A mixture of 150 mL of the catalyst 2 and 90 mL of alumina balls having an outer diameter of 5 mm was filled into an inlet part for a raw material gas of the same fixed bed tube type reactor as used in Example 1, and a mixture of 200 mL of the catalyst 2 and 40 mL of alumina balls having an outer diameter of 5 mm was filled into a middle part of this reactor, and 1020 mL of the catalyst 2 was filled into an outlet part of this reactor. A length of the catalyst bed at this time was 3005 mm. The same raw material gas as used in Example 1 was passed through this catalyst bed under the same conditions.

Upon measuring a temperature of the catalyst bed, a first high temperature zone in which the maximum temperature point was 180 mm from an end of the inlet side of the raw material gas, a second high temperature zone in which the maximum temperature point was 620 mm from the end of the inlet side of the raw material gas, and a third high temperature zone in which the maximum temperature point was 1100 mm from the end of the inlet side of the raw material gas were observed. That is, among the above three adjacent high temperature zones, a ratio of a distance between the first and the second high temperature zones to the length of the catalyst bed was 0.15, and a ratio of a distance between the second and the third high temperature zones to the length of the catalyst bed was 0.16. In addition, ΔT at the maximum temperature of the first high temperature zone was 16° C., ΔT at the maximum temperature of the second high temperature zone was 18° C., and ΔT at the maximum temperature of the third high temperature zone was 17° C. Further, ΔT at a position 480 mm from the end of the inlet side for the raw material gas was 9° C., and ΔT at a position 960 mm from the end of the inlet side for the raw material gas was 9° C.

Table 1 shows results of analysis of the reaction product.

TABLE 1

| Examples, Comparative Examples | Conversion of Methacrolein (%) | Selectivity of Methacrylic acid (%) | Yield of Uni-flow Methacrylic acid (%) |
|---|---|---|---|
| Example 1 | 84.5 | 84.0 | 71.0 |
| Comparative Example 1 | 85.7 | 81.9 | 70.2 |
| Comparative Example 2 | 87.9 | 78.1 | 68.6 |
| Comparative Example 3 | 87.3 | 78.3 | 68.4 |
| Comparative Example 4 | 86.3 | 79.5 | 68.6 |
| Example 2 | 85.2 | 85.4 | 72.8 |

INDUSTRIAL APPLICABILITY

According to the present invention, when synthesizing methacrylic acid by filling a solid oxidation catalyst into a fixed bed tube type reactor provided with a heat medium bath and by flowing a raw material gas containing methacrolein and oxygen through the catalyst bed, methacrylic acid can be manufactured in high yields by providing two or more high temperature zones in which each ΔT is 15 to 35° C. without providing any sections in which ΔTs exceed 35° C.

Also, according to the present invention, the yields are further increased by providing a first high temperature zone and a second high temperature zone from an inlet side for the raw material gas in such a manner that a distance between these high temperature zones is 0.2 to 0.9 times an overall length of the catalyst bed.

Further, the yields are also increased by employing a composite oxide represented by the above described formula (1) as a solid oxidation catalyst.

What is claimed is:

1. A method for manufacturing methacrylic acid, comprising:

passing a raw material gas containing methacrolein and oxygen through a catalyst bed of a solid oxidation catalyst in a fixed bed tube type reactor that is immersed in a heat medium bath, thereby oxidizing the methacrolein to methacrylic acid, wherein the catalyst bed does not have any sections in which the temperature difference between the temperature of the heat medium bath and the temperature of the catalyst bed {ΔT=(catalyst bed temperature)−(heat medium bath temperature)} exceeds 35° C. but does have at least two high temperature zones wherein the temperature of each of said zones falls within the temperature region of 15 to 35° C. above the temperature of the heat medium bath.

2. The method for manufacturing methacrylic acid according to claim 1, wherein the distance between a first high temperature zone and a second high temperature zone within the solid oxidation catalyst bed of the reactor taken from the inlet of the reactor through which the raw material gas enters the reactor is 0.2 to 0.9 times the overall length of the catalyst bed.

3. The method for manufacturing methacrylic acid according to claim 1, wherein said solid oxidation catalyst is a composite oxide represented by formula (1):

$$Mo_aP_bCu_cV_dX_eY_fO_g \qquad (1)$$

wherein Mo, P, Cu, V and O represent molybdenum, phosphorus, copper, vanadium, and oxygen, respectively, X represents at least one element selected from the group consisting of iron, cobalt, nickel, zinc, magnesium, calcium, strontium, barium, titanium, chromium, tungsten, manganese, silver, boron, silicon, tin, lead, arsenic, antimony, bismuth, niobium, tantalum, zirconium, indium, sulfur, selenium, tellurium, lanthanum, and cerium, and Y represents at least one element selected from the group consisting of potassium, rubidium, cesium, and thallium, wherein a, b, c, d, e, f and g represent atomic amounts of the respective elements, and when a=12, $0.1 \leq b \leq 3$, $0.01 \leq c \leq 3$, $0.01 \leq d \leq 3$, $0 \leq e \leq 3$ and $0.01 \leq f \leq 3$, g is the amount of oxygen which is required to satisfy the summed valences of the Mo, P, Cu, V, X and Y components.

4. The method for manufacturing methacrylic acid according to claim 2, wherein said solid oxidation catalyst is a composite oxide represented by formula (1):

$$Mo_aP_bCu_cV_dX_eY_fO_g \qquad (1)$$

wherein Mo, P, Cu, V and O represent molybdenum, phosphorus, copper, vanadium, and oxygen, respectively, X represents at least one element selected from the group consisting of iron, cobalt, nickel, zinc, magnesium, calcium, strontium, barium, titanium, chromium, tungsten, manganese, silver, boron, silicon, tin, lead, arsenic, antimony, bismuth, niobium, tantalum, zirconium, indium, sulfur, selenium, tellurium, lanthanum, and cerium, and Y represents at least one element selected from the group consisting of potassium, rubidium, cesium, and thallium, wherein a, b, c, d, e, f and g represent atomic amounts of the respective elements, and when a=12, $0.1 \leq b \leq 3$, $0.01 \leq c \leq 3$, $0.01 \leq d \leq 3$, $0 \leq e \leq 3$ and $0.01 \leq f \leq 3$, g is the amount of oxygen which is required to satisfy the summed valences of the Mo, P, Cu, V, X and Y components.

5. The method for manufacturing methacrylic acid according to claim 1, wherein said temperature difference ΔT and the temperatures of the high temperature zones are controlled by adjusting the activity of the catalyst per unit volume within said catalyst bed.

6. The method for manufacturing methacrylic acid according to claim 2, wherein said temperature difference ΔT and the temperatures of the high temperature zones are controlled by adjusting the activity of the catalyst per unit volume within said catalyst bed.

7. The method for manufacturing methacrylic acid according to claim 3, wherein said temperature difference ΔT and the temperatures of the high temperature zones are controlled by adjusting the catalytic activity per unit volume within said catalyst bed.

8. The method for manufacturing methacrylic acid according to claim 4, wherein said temperature difference ΔT and the temperatures of the high temperature zones are controlled by adjusting a catalytic activity per unit volume within said catalyst bed.

9. The method for manufacturing methacrylic acid according to claim 2, wherein the distance between a first high temperature zone and a second high temperature zone within the solid oxidation catalyst bed of the reactor taken from the inlet of the reactor through which the raw material gas enters the reactor is 0.25 to 0.8 times the overall length of the catalyst bed.

10. The method for manufacturing methacrylic acid according to claim 1, wherein the position of the first high temperature zone (ΔT is maximum) within the solid oxidation catalyst bed of the reactor taken from the inlet of the reactor is at a distance of 0 to 0.7 times the overall length of the solid oxidation catalyst bed.

11. The method for manufacturing methacrylic acid according to claim 10, wherein the position of the first high temperature zone (ΔT is maximum) within the solid oxidation catalyst bed of the reactor taken from the inlet of the reactor is at a distance of 0.1 to 0.5 times the overall length of the solid oxidation catalyst bed.

* * * * *